(12) United States Patent
Faber

(10) Patent No.: US 8,262,632 B2
(45) Date of Patent: Sep. 11, 2012

(54) FEMALE URINARY CATHETERIZATION DEVICE

(76) Inventor: Robert Branch Faber, Nashville, TN (US)

(*) Notice: Subject to any disclaimer, the term of this patent is extended or adjusted under 35 U.S.C. 154(b) by 275 days.

(21) Appl. No.: 12/420,033

(22) Filed: Apr. 7, 2009

(65) Prior Publication Data

US 2010/0256580 A1 Oct. 7, 2010

(51) Int. Cl.
*A61F 5/44* (2006.01)
*A61M 25/00* (2006.01)
*A61B 5/00* (2006.01)

(52) U.S. Cl. ........ 604/329; 604/328; 604/330; 604/528; 600/574

(58) Field of Classification Search .................. 604/329, 604/330, 331, 328; 600/574
See application file for complete search history.

(56) References Cited

U.S. PATENT DOCUMENTS

| | | | | |
|---|---|---|---|---|
| 3,347,238 A * | 10/1967 | Gresham | ........................ | 604/329 |
| 3,528,423 A * | 9/1970 | Lee | ................................ | 604/329 |
| 3,815,581 A * | 6/1974 | Levin | ............................. | 600/574 |
| 4,023,560 A * | 5/1977 | Cade et al. | ..................... | 600/574 |
| 4,117,847 A * | 10/1978 | Clayton | ....................... | 604/97.01 |
| 4,246,901 A * | 1/1981 | Frosch et al. | .................. | 604/329 |
| 4,690,677 A * | 9/1987 | Erb | ................................. | 604/329 |
| 4,846,818 A * | 7/1989 | Keldahl et al. | ................. | 604/329 |
| 4,986,823 A * | 1/1991 | Anderson et al. | ............. | 604/329 |
| 5,045,078 A * | 9/1991 | Asta | ............................... | 604/329 |
| 5,084,036 A * | 1/1992 | Rosenbaum | ................... | 604/329 |
| 5,653,700 A * | 8/1997 | Byrne et al. | ................... | 604/329 |
| 5,795,288 A * | 8/1998 | Cohen et al. | .................... | 600/29 |
| 6,183,454 B1 * | 2/2001 | Levine et al. | ................. | 604/329 |
| 6,398,742 B1 * | 6/2002 | Kim | .............................. | 600/574 |
| 6,428,521 B1 * | 8/2002 | Droll | .............................. | 604/329 |
| 6,544,240 B1 * | 4/2003 | Borodulin et al. | ............ | 604/329 |
| 6,592,560 B2 * | 7/2003 | Snyder | ........................... | 604/331 |
| 7,104,980 B1 * | 9/2006 | Laherty et al. | ................. | 604/528 |
| 2001/0031952 A1 * | 10/2001 | Karram et al. | ................. | 604/344 |
| 2001/0037098 A1 * | 11/2001 | Snyder | ........................... | 604/331 |
| 2009/0088786 A1 * | 4/2009 | Zook et al. | ..................... | 606/170 |
| 2011/0028922 A1 * | 2/2011 | Kay et al. | ...................... | 604/329 |

* cited by examiner

*Primary Examiner* — Susan Su
(74) *Attorney, Agent, or Firm* — Ataullah Arjomand

(57) ABSTRACT

Disclosed is a catheter guide for female self-catheterization to assist in guiding a catheter into the user's urethra. The catheter guide includes a hand-held guide with a vaginal insert portion joined to a handle at a fixed or an adjustable angle. There is an enclosed or open canal in the vaginal insert portion which can be aligned with the urethra, when the insert portion is in the vagina, and through which a catheter can be guided into the urinary tract.

8 Claims, 4 Drawing Sheets

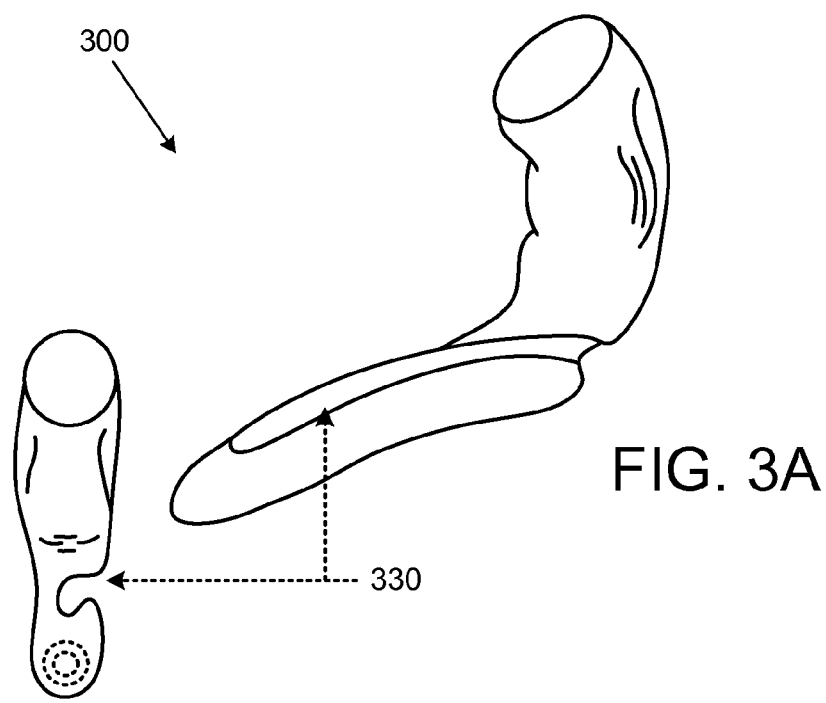
FIG. 3A
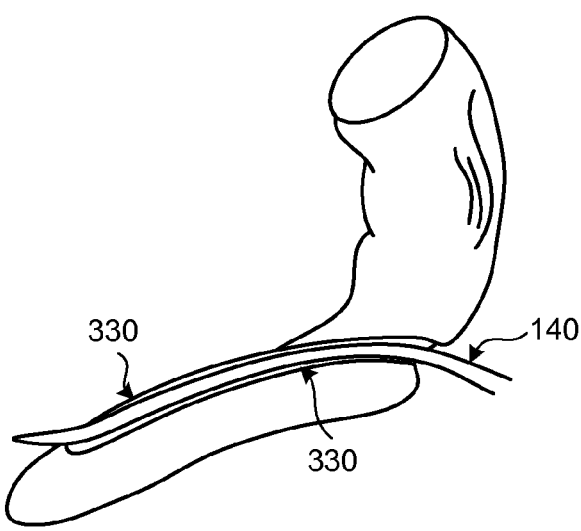
FIG. 3B
FIG. 3C

FEMALE URINARY CATHETERIZATION DEVICE

FIELD OF THE INVENTION

Disclosed invention relates to medical devices for use in cases of urinary abnormalities and, more specifically, to a portable catheter for assisting in the process of intermittent female self-catheterization.

BACKGROUND

The bladder serves two functions: for storage of urine and evacuation of urine. If a bladder cannot function as a reservoir to retain urine, the problem is known as incontinence. Conversely, if a bladder is unable to evacuate urine, the problem is called urinary retention.

One solution is to use somewhat ineffective and expensive drugs and medications. Another solution is an indwelling Foley catheter which is uncomfortable and can lead to urinary tract infections. The Foley catheter has an expansible ring-like balloon at the distal end. The catheter would be inserted into the bladder through the urethra, and then the balloon would be expanded sufficiently to prevent withdrawal without first deflating the balloon. With this catheter, urine could continuously drain from the bladder through openings in the distal end of the catheter and subsequently through a drain tube.

While such catheters are successful in draining urine, they present a number of problems. Great care must be taken when moving the person using these catheters to prevent accidental pulling and partial withdrawal of the catheter or over-inserting it, which severely limits the mobility of the user. Care and skill are also required in inserting and removing the catheter to assure that the proper length is inserted, the balloon is expanded to the proper extent, and the balloon is fully deflated prior to removal.

Yet another solution to some urinary problems is self intermittent catheterization (SIC), where the female patient catheterizes herself several times a day. It is safe, simple, and has the lowest risk of infection. Unfortunately, because of the anatomical location of the opening of the female urethra it is difficult to perform SIC. This is especially true in the obese patients or the physically handicapped. On the whole, intermittent self-catheterization is difficult if not impossible, because the process generally requires the patient to have fine motor skills and good vision to locate the urethra.

The U.S. Pat. No. 5,045,078, granted to Linda R. Asta, discloses an apparatus to assist in guiding a catheter into the urinary meatus. Asta's apparatus is comprised of a vaginal insert and a handle and has at least one guide or alignment hole on its handle. The guide hole of the handle is alignable with the urinary meatus when the insert portion is in the vagina. To effectively use Asta's apparatus, the user needs to completely insert the vaginal insert in her vagina and hope for the guide hole to be aligned with her urethra. However, if its guide hole does not align with her urinary meatus, there is no provision for maneuvering the catheter into the urinary meatus. Asta suggests having multiple alignment holes or a single movable alignment hole on her apparatus' handle, but these embodiments have the same shortcomings as Asta's embodiment with a single hole.

Additionally, while Asta suggests the possibility of using a Foley-type catheter with her device, it is not possible to pass the tip of any Foley catheter through her guide holes as they are disclosed and illustrated in her patent. And, if her guide holes are so large that a Foley catheter can pass through them, then such holes cannot be used for guiding a catheter into the user's urethra.

In general, for the reasons mentioned and more, the existing solutions to urinary abnormalities are not very satisfactory.

BRIEF DESCRIPTION OF THE DRAWINGS

FIGS. 3A, 3B, and 3C illustrate another embodiment of the invention in which the guide channel is an open canal, into which a catheter can enter from its side opening.

DETAILED DESCRIPTION

The described embodiments herein increase the potential and possibility for intermittent self-catheterization by those women with, for example, neuromuscular dysfunctions or complications resulting from other urinary disorders which require the process of intermittent self-catheterization to aid in the function of micturition. The proposed embodiments describe a catheter guide for use during female intermittent self-catheterization for the purpose of assisting in guiding a catheter into the urinary meatus.

While several details have been discussed in this section, one skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 1A:
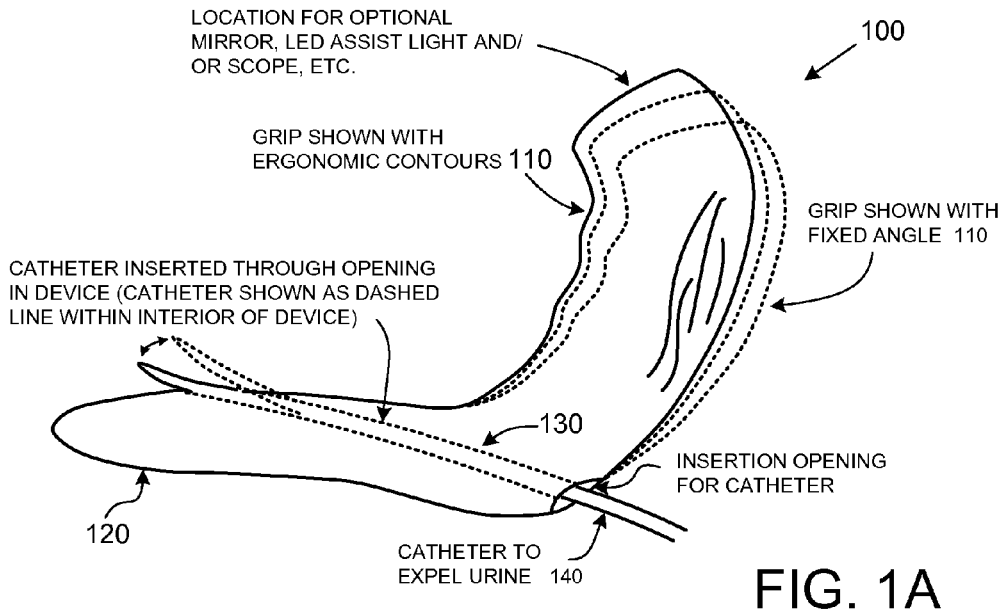
FIGS. 1A and 1B illustrate a catheter guide that comprises a handle and a vaginal insert according to an embodiment of the invention, wherein the vaginal insert has a guide channel/canal through it.
Figure 1B:
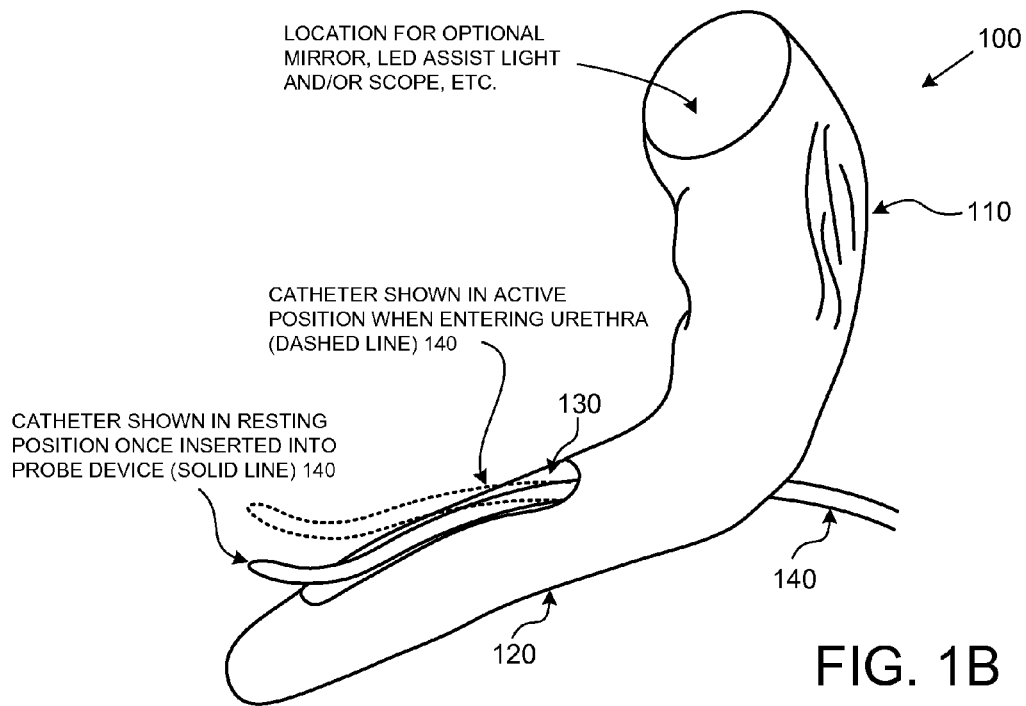

FIGS. 1A and 1B are illustrations of an embodiment of the catheter guide 100. It is a self contained, single or multi piece, disposable or reusable apparatus which has a handle 110 and uses a vaginal orifice/insert 120 with a guide canal 130 which acts as a template to guide the catheter 140 into the urethra and the bladder. The catheter guide 100 may be made of any surgically acceptable material, such as plastic, and its structure may be rigid or flexible. The catheter guide 100, in its entirety or partially, may be constructed as a hollow or solid structure, or a combination thereof, to reduce weight and/or cost.

In the embodiment of FIGS. 1A and 1B, the guide channel 130 is an enclosed conduit and the catheter 140 enters it from one end and exits from the other end. The vaginal insert portion 120 may have any suitable shape that can comfortably enter the vagina. In one embodiment the vaginal insert portion 120 may have oval or circular cross-sections which decrease in dimensions as the cross-sections approach the tip of the vaginal insert portion 120.

Typically, the anatomical location of the urethral opening with respect to the top of the vaginal orifice is about 0.5 to 0.75 centimeters and the length of the female urethra is also 2.5 to 3.0 centimeters. The disclosed apparatus utilizes this anatomical relationship to aid the patient in catheterizing herself. The catheter 140 is placed within the guiding channel 130 and as the vaginal insert 120 enters into the vagina and advances into the vaginal canal, the catheter 140 is directed into the urethral opening, the urethra, and subsequently into the bladder. It is simple, painless, and it does not require direct observation or manual dexterity.

In some embodiments the handle 110, the vaginal insert 120, or both may include, for example, a mirror, a light, a scope, a camera, a sensor, a measurement apparatus, etc., or a combination thereof. Such additional components on the handle 110 and/or the vaginal insert 120 will help the user to better locate her urinary meatus and to easily insert the catheter into her urethra and/or help her with her other needs. FIG. 1A shows a mirror attached to one end of the handle 110.

The detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Figure 2:
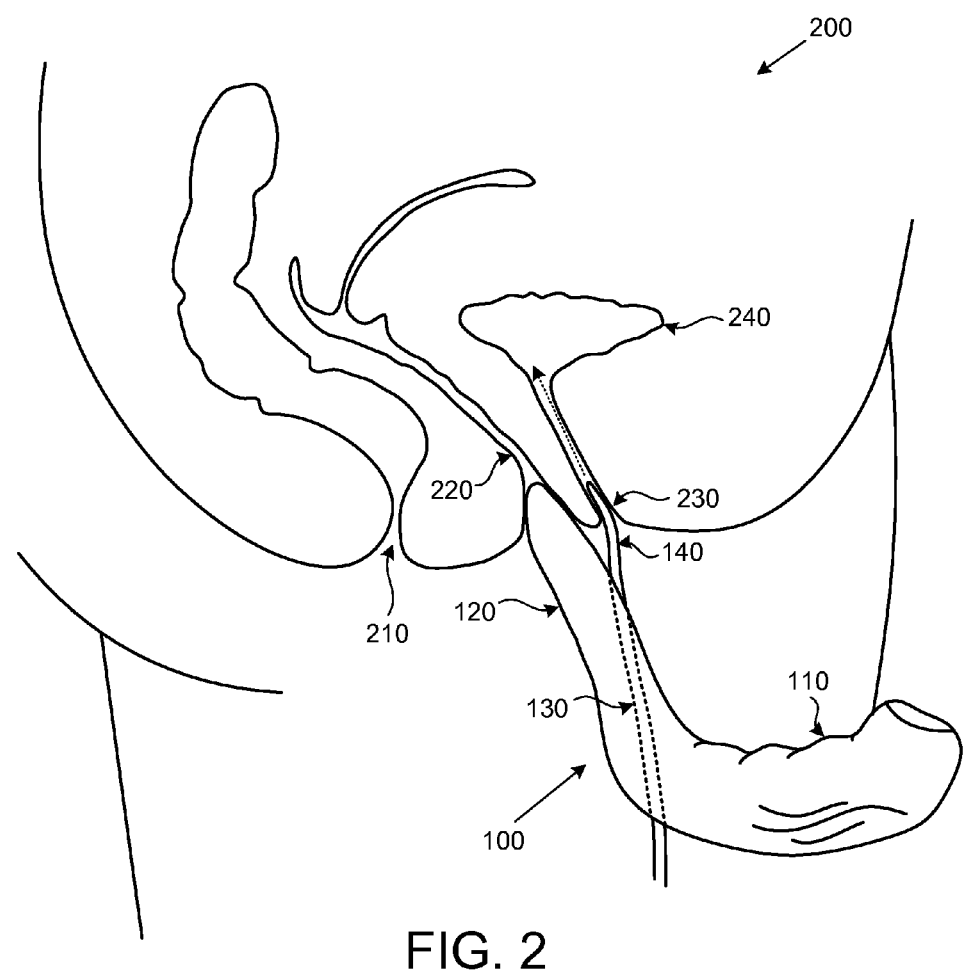
FIG. 2 illustrates the embodiment of FIG. 1, where the catheter guide is in an inserted position.

FIG. 2 shows an embodiment of the catheter guide 100 in an inserted position 200, with the vaginal insert 120 in the vagina 220. This is shown in a position relative to the rectum 210, the uterus 230 and the bladder 240. In FIG. 2, the catheter 140, the end of which passes through the guide canal 130 of the vaginal insert 120, enters into the urinary meatus, and through the urethra into the bladder. Catheter 140 may be a Foley-type catheter or a plastic type urethral catheter.

In one embodiment the guide channel 130 is wider than the catheter 140 and the user of the apparatus can wiggle the catheter 140 to enter it into the urethral opening. In another embodiment the inside diameter of the guide channel 130 is substantially the same as the outside diameter of the catheter 140 and the user of the apparatus can align the catheter 140 with the urethral opening 230 by small movements of the apparatus, for example, in and out of vagina.

In general, a method of using these apparatus may be described as follows: 1) the patient gently spreads her legs; 2) cleans her vaginal introitus; 3) lubricates the tip of the vaginal insert portion 120 and the tip of the catheter 140; 4) places the tip of the vaginal insert portion 120 into her vaginal opening with the handle 110 pointed upward; 5) advances the catheter guide 100 into the vaginal canal. This device, using the vaginal canal as a template, directs the catheter into the urethra. If the catheter 140 does not enter the urethra at once, patient can wiggle the catheter 140 or the catheter guide 100 to insert the catheter 140 into her urethra. The bladder then empties under gravity; and 6) the patient withdraws the device and completes the catheterization process.

FIGS. 3A, 3B, and 3C illustrate another embodiment 300, in which the guide channel 330 is an open canal, as opposed to the enclosed channel 130 of FIGS. 1A and 1B, and the catheter 140 can enter its entire length from the side. In some embodiments the guide channel may be a combination of these configurations. The catheter guide 300 can be used to guide a conventional Foley catheter or any Foley-type catheter into the patient's urethra and the bladder since such catheters, because of the size of their tips, cannot enter from an end-opening of an enclosed channel such as channel 130 of FIG. 1A or enter the guide hole(s) of U.S. Pat. No. 5,045,078. As a catheterizing device, this embodiment can utilize any catheter on the market such as the Foley catheter.

To use catheter guide 300, the Foley catheter is simply clipped to or inserted into the guide channel 330 from its open side, after which the patient can use the vaginal canal as a template to direct the catheter into the bladder. The procedure is identical to the SIC mentioned above. After the catheter is inserted into the bladder and urine flows through the catheter, the user can inflate the Foley balloon to secure the catheter's position in the bladder. She then unclips or pulls out the catheter from the open side of the device 300 and completes the catheterization.

Figure 4:
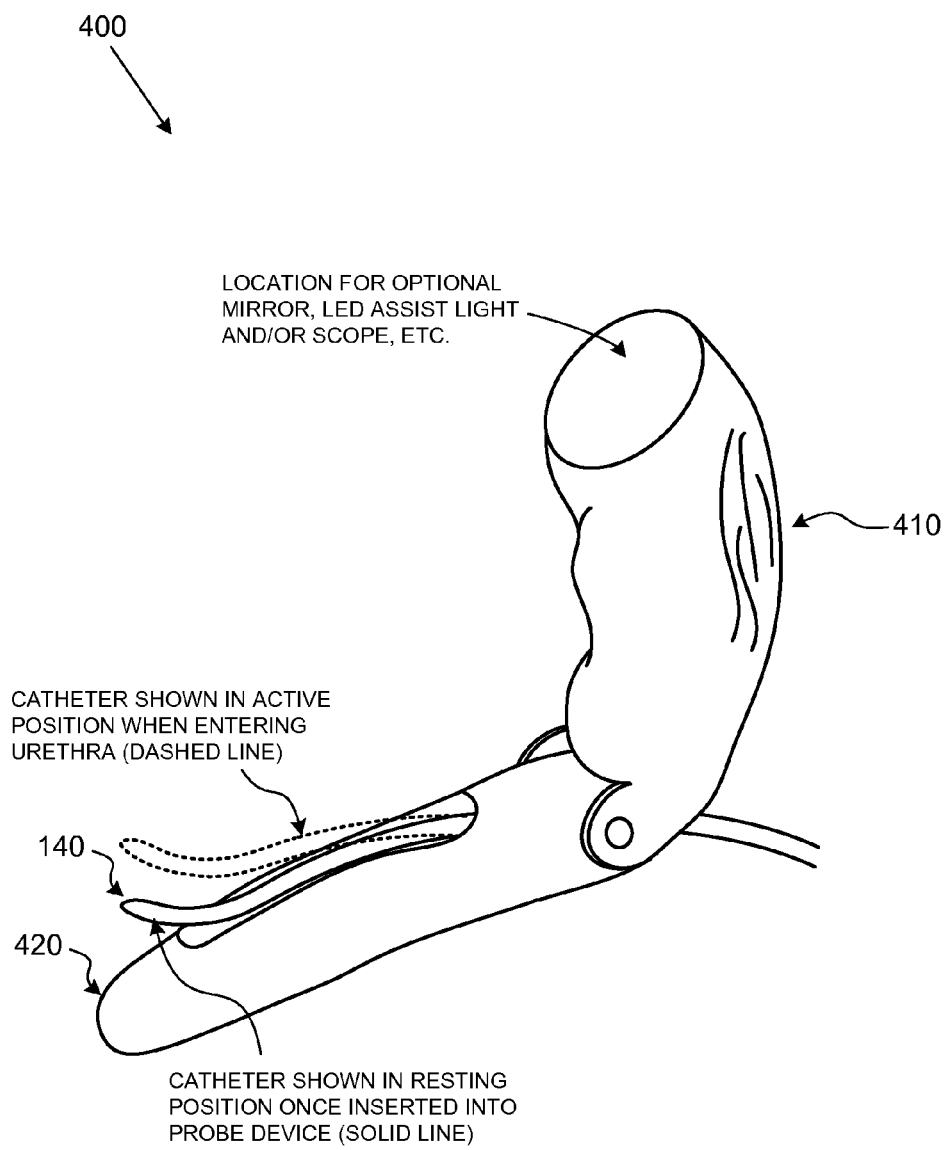
FIG. 4 illustrates yet another embodiment of the catheter guide where the angle between the handle and the vaginal insert portion is adjustable.

FIG. 4 illustrates yet another embodiment of the catheter guide 400 where the angle between the handle 410 and the vaginal insert portion 420 is adjustable. In this embodiment the handle 410 may be hinged to the vaginal insert portion 420 and be kept in any desired position, with respect to the vaginal insert 420, by friction or by any other means known in mechanical arts. Such arrangement makes the apparatus adaptable to different users' physical makeup and flexibility.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

The above detailed description of the embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize.

The teachings provided herein can be applied to other apparatus and systems, not necessarily the system described herein. The elements and acts of the various embodiments described above can be combined to provide further embodiments.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

I claim:

1. A self-catheterization apparatus to assist in guiding a catheter into the urinary meatus of a female user, the apparatus comprising:
   a catheter having longitudinal axis;
   a handle portion for handling the apparatus; and
   a vaginal insert portion, wherein the handle portion and the vaginal insert portion constitute opposite ends of the apparatus and wherein the vaginal insert portion includes a channel disposed along a surface thereof, said channel is configured to align the catheter with the urinary meatus and comprises a single longitudinal opening along an entire length of the channel, said opening configured to allow the catheter to be inserted into the channel in a direction transverse to the longitudinal axis,
   wherein the vaginal insert is configured to be positioned partially or completely in the vagina.

2. The apparatus of claim 1, wherein the angle between the handle and the vaginal insert portion is adjustable.

3. The apparatus of claim 1, wherein the handle portion includes a mirror, a light, a scope, a camera, a sensor, a measurement apparatus, or a combination thereof.

4. The apparatus of claim 1, wherein the vaginal insert portion includes a minor, a light, a scope, a camera, a sensor, a measurement apparatus, or a combination thereof.

5. An apparatus configured to assist in guiding a catheter into a urethra of a user, the apparatus comprising:
   a urethral catheter having a longitudinal axis;
   a handle portion for handling the apparatus; and
   a positioning portion, wherein the handle portion and the positioning portion are joined at a point and wherein the positioning portion includes a canal disposed along a surface thereof, said canal is configured to align the catheter with the urethra and comprises a single longitudinal opening from one end of the canal all the way to the other end of the canal, said opening configured to allow the catheter to be inserted into the canal in a direction transverse to the longitudinal axis,
   wherein the positioning portion is configured to be positioned partially or completely in a body cavity near the urethra when the user inserts the catheter into the urethra.

6. The apparatus of claim 5, wherein an angle between the handle and the positioning portion is adjustable.

7. The apparatus of claim 5, wherein the handle portion includes a mirror, a light source, a scope, a camera, a sensor, a measurement apparatus, or a combination thereof.

8. The apparatus of claim 5, wherein the positioning portion includes a mirror, a light source, a scope, a camera, a sensor, a measurement apparatus, or a combination thereof.

* * * * *